(12) United States Patent
Coroneo

(10) Patent No.: US 6,372,449 B1
(45) Date of Patent: Apr. 16, 2002

(54) OPTHALMIC METHODS AND USES

(76) Inventor: Minos Theodore Coroneo, 2 St. Pauls Street, Randwick, New South Wales (AU), 2031

( * ) Notice: Subject to any disclaimer, the term of this patent is extended or adjusted under 35 U.S.C. 154(b) by 0 days.

(21) Appl. No.: 09/438,448

(22) Filed: Nov. 12, 1999

(51) Int. Cl.$^7$ .......................... A01N 1/30; A01N 33/26; A61K 49/00; A61B 13/00
(52) U.S. Cl. ...................... 435/40.5; 424/9.1; 514/150; 600/558
(58) Field of Search ...................... 435/4, 40.5; 606/4, 606/558; 424/9.1; 514/150

(56) References Cited

PUBLICATIONS

Medline Acc No. 72009521. Matsusaka (1971). The fine structure of the inner limiting membrane of the rat retina as revealed by ruthenium red staining. Journal of Ultrastructure Research 36(3): 312–317.*

Melles et al. (1999). Trypan blue capsule staining to visualize the capsulorhexis in cataract surgery. J Cataract Refract Surg 25(1), pp 7–9.*

Sulzer et al. (1986). Alcian blue and neutral red staining of retinal synaptic layers. J Histochem Cytochem 34(11), pp 1513–1515.*

Caplus abstract (Acc. no 1982:403080). Liu et al. (1981). Vital staining of ocular tissue by injecting trypan blue into the anterior chamber. Nippon. Ganka Kiyo 32(7), pp 1630–7.*

Norn (1980). Per operative trypan blue vital staining of corneal endothelium. Acta Ophtamol (Copenhagen) 58(4); pp 550–555.*

* cited by examiner

Primary Examiner—Ralph Gitomer
Assistant Examiner—Mahreen Chaudhry
(74) Attorney, Agent, or Firm—Foley & Lardner

(57) ABSTRACT

Ophthalmic membranes and uses are described. Intraocular membranes and structures within the eye are identified by instilling into the eye a trypan blue solution which marks in a visually identifiable manner intraocular membranes and structures within the eye.

7 Claims, No Drawings

OPTHALMIC METHODS AND USES

FIELD OF THE INVENTION

The present invention relates to ophthalmic methods and uses, more particularly to the identification of intraocular membranes and structures within the eye as an aid to diagnosis and treatment.

BACKGROUND OF THE INVENTION

The identification of membranes within the eye, whether pathogenic in origin, or membranes normally found within the eye, is difficult due to the opaque nature of such membranes. As such membranes cannot be readily visualized, the diagnosis and treatment of various conditions associated with ocular membranes is hampered. Structures within the eye, such as the trabecular meshwork which may be implicated in glaucoma, are difficult to visualize, again due to their opaque nature or lack of pigmentation. Hence, a physician or surgeon diagnosing or treating conditions associated with membranes in the eye, with eye structures, or believed to be associated with structures of the eye is hampered by the inability to properly visualize such structures.

In the development of machine-human interfaces to ameliorate vision problems, such as partial or complete blindness (such as a "bionic eye"), it may be necessary to attach a device such as a transparent membrane to the retina to allow signal transduction across the membrane. Because of the transparency requirement of such devices it is exceedingly difficult to attach or otherwise associate them with the retina or other structures.

It is an object of the present invention to address prior art limitations in the identification of intraocular membranes and structures within the eye as an aide to diagnosis and surgery.

BRIEF SUMMARY OF THE INVENTION

In a first aspect of this invention there is provided a method for the identification of intraocular membranes and structures within the eye, which comprises instilling into the eye a trypan blue solution which solution marks in a visually identifiable manner intraocular membranes and structures within the eye. Once visualized, diagnosis and surgical treatment can take place in a greatly facilitated manner compared with the prior art.

In accordance with a further aspect of this invention there is provided a method for the identification of pathological membranes within the eye, which comprises instilling into the eye a trypan blue solution which solution marks in a visually identifiable manner the pathological membranes in a manner which allows their ready identification and surgical removal.

In accordance with a further aspect of the invention there is provided a method for the identification of intraocular structures which comprises instilling into the eye a solution of trypan blue solution, which solution marks in a visually identifiable manner structures within the eye this allowing ready identification of such structures for diagnosis and/or treatment.

In accordance with a further aspect of this invention there is provided a method for introducing a transparent device into the eye which comprises incubating the device with a trypan blue solution so as to mark the device an identifiable color, and thereafter introducing into the eye the device, said visualization of the device allowing accurate positioning of the device within the eye.

In accordance with a still further aspect of this invention there is provided use of trypan blue in the manufacture of a composition to visually identify intraocular membranes and structures within the eye.

DETAILED DESCRIPTION OF THE INVENTION

This invention utilizes trypan blue in methods of identifying intraocular membranes and structures within the eye, and for the purposes of visualizing devices to be introduced into the eye.

Trypan blue is a widely available dye, which has been used in medical applications for many years. It is FDA approved for in vivo and in vitro uses. Trypan blue solutions are preferably freshly prepared at the time of use. In this regard, trypan blue powder may be mixed with an ocularly compatible solution for instillation into the eye. This may be conveniently achieved by a two chamber unit containing dry trypan blue (in powder form) in one chamber, and an ocularly compatible solution in the other chamber, for example separated by openable barrier means such as a rubber stopper, such that on mixing after opening the barrier means and ocularly compatible solution is prepared and can be introduced into the eye. Of course, trypan blue solutions may be produced by standard techniques in the art of formulation chemistry. Generally, trypan blue solutions contain trypan blue in an amount of from 0.05% to 3% w/w, more preferably 0.1% to 1.5% w/w, still more preferably between 0.1% and 0.3% w/w.

Trypan blue solutions may be stored, for example, according to established procedures for storage of solutions for medical use. Compositions are generally isotonic. For introduction into the eye, the solutions are sterile, buffered and free of particulate material. Any ocularly compatible solution may be used. An example of a suitable solution includes physiological saline.

In a first aspect of the invention there is provided a method for the identification of intraocular membranes and structures within the eye, which comprises instilling into the eye a trypan blue solution which solution marks in a visually identifiable manner intraocular membranes and structures within the eye.

Peeling of epiretinal and internal limiting membrane of the retina is particularly difficult due to the transparent nature of such membranes, and is part of the surgical management of premacular fibrosis and macular hole. In severe diabetic retinopathy in particular and with proliferative vitreoretinopathy (PVR) in general, excision of membranes can be difficult partly because of problems with defining the extent of the membranes.

Pathological membranes may arise in the eye which occlude vision and/or are painful or irritating to the effected subject. Such membranes are often extremely difficult to visualize presenting difficulties in diagnosis and surgical treatment for membrane removal.

In respect of retinal surgery for the removal of aberrant membranes or for the peeling of epiretinal and internal limiting membranes of the retina, the vitreous gel of the eye is removed by a technique known as pars plana vitrectomy, with stripping of the outer (cortical) vitreous. In place of the vitreous gel, infusion fluid is introduced into the eye via an infusion port. The inner limiting membrane may then be stained with trypan blue solution (for example 0.1% w/w) instilled with a fine silicone-tipped extrusion needle, left for 30 seconds to stain the membrane, aspirated, followed by irrigation of the area with balanced salt (physiological)

solution. Peeling of the membrane proceeds and is greatly facilitated because of improved visualization of the extent of the membrane. The procedure is then completed in standard fashion with fluid-gas exchange.

In respect of other membranes in the eye, whether of pathological origin or normally occurring within the eye, trypan blue solution is instilled into the eye in the area of the membrane or the suspected area of the membrane occurrence. After a period of time wherein the membrane is stained or marked, the trypan blue solution is removed, and the area generally irrigated to remove excess trypan blue. Identification of membranes can then be made by visual analysis, and surgical removal can then proceed according to established techniques if so desired.

Eye pressure is regulated in part by flow of ocular fluid (aqueous humour) through a biological valve, known as the trabecular meshwork. In glaucoma, a pathological condition where the eye pressure is raised, the eye pressure may be lowered by application of a laser energy source to the trabecular meshwork. In the prior art the success of this technique generally depends upon the presence of sufficient natural pigmentation of the trabecular meshwork which will absorb the laser energy. Using trypan blue to mark the trabecular meshwork improves identification of this structure, and the uptake of laser energy. A trypan blue solution is instilled into the eye in the location of the trabecular meshwork, and after a short time period such as from 10 seconds to one minute, the trypan blue solution is removed and the area generally irrigated to remove excess trypan blue. The now marked trabecular meshwork can be readily visually distinguished, and laser application can take place. Other ocular structures may be marked in the same manner so as to enable identification and if necessary surgical or other treatment.

Accordingly, in a further aspect of this invention there is provided a method for the identification of pathological membranes within the eye, which comprises instilling into the eye a trypan blue solution which solution marks in a visually identifiable manner the pathological membranes in a manner which allows their ready identification and surgical removal.

In another aspect of this invention there is provided a method for the identification of intraocular structures which comprises instilling into the eye a solution of trypan blue solution, which solution marks in a visually identifiable manner structures within the eye this allowing ready identification of such structures for diagnosis and/or treatment.

Machine-human interfaces may be used to ameliorate vision problems, such as partial or complete blindness. Such devices may be a transparent membrane which is attached to the retina to allow single transduction across the membrane thus providing stimulating of the optic nerve. The membrane may contain a circuit layout or other intelligent component which assists in the visual process. As such devices are generally transparent, there is the problem of accurately positioning the device within the eye such as on or in association with the retina. By incubating such device with a trypan blue containing solution, the device may be marked in a visually detectable manner, and thereafter introduced into the eye to allow accurate positioning therein.

In accordance with a further aspect of this invention there is provided a method for introducing a transparent device into the eye which comprises incubating the device with a trypan blue solution so as to mark the device an identifiable color, and thereafter introducing into the eye the device, said visualization of the device allowing accurate positioning of the device within the eye.

A number of dyes have been used in the eye to identify vital structures, examples of dyes used include indocyanin green, rose bengal, gentian violet and methylene blue. All of these dyes are toxic to ocular structures, may permanently stain elements within the eye, and may possess various side effects. Surprisingly, trypan blue allows ready visualization of membranes and structures within the eye, is non-toxic, does not irreversibly stain eye structures, and is very convenient to use and administer.

In accordance with a still further aspect of this invention there is provided use of trypan blue in the manufacture of a composition to visually identify intraocular membranes and structures within the eye.

An embodiment of the invention will now be described with reference to the following non-limiting examples.

EXAMPLE 1

Patient A

Patient A required peeling of epiretinal and internal limiting membrane of the retina as part of the surgical management of premacular fibrosis and macular hole conditions.

Patient B

Patient B is a diabetic suffering from severe diabetic retinopathy, with proliferative vitreo retinopathy.

A 0.1% w/w solution of trypan blue in physiological saline is prepared.

Surgical Procedure

In each patient the vitreous gel of the eye is removed by pars plana vitrectomy an established procedure in the art, which involves stripping of the outer (cortical) vitreous. In place of the vitreous gel an infusion fluid is introduced to maintain the pressure within the eye and prevent collapse of the eye. The inner limiting membrane is stained with a 0.1% trypan blue solution instilled with a fine silicon-tipped extrusion needle, left for 30 seconds so as to mark the membrane, the area is then aspirated and then irrigated with a balanced physiological salt solution. The membranes in question are readily identified and allow peeling or removal through the ready visualization. Following the appropriate surgical procedure, fluid-gas exchange takes place.

EXAMPLE 2

Patient C

Patient C is a glaucoma sufferer who has elevated eye pressure. 0.1% trypan blue is instilled into the eye of patient C through a cannular, introducing the trypan blue solution in the area with trabecular meshwork. The trabecular meshwork is then visualized by simple visual identification in contrast to the situation where the trabecular meshwork was not visually identifiable prior to trypan blue instillation. After removal of excess trypan blue by irrigation of the area with a balanced physiological salt solution, the area is subject to laser light, this improving uptake of laser energy. Successful lowering of eye pressure results.

Throughout this specification and the claims which follow, unless the context requires otherwise, the word "comprise", or variations such as "comprises" or "comprising", will be understood to imply the inclusion of a stated integer or step or group of integers or steps but not the exclusion of any other integer or step or group of integers or steps.

What is claimed is:

1. A method for the identification of intraocular membranes and structures within the eye, which comprises instilling into the eye a trypan blue solution which solution marks in a visually identifiable manner intraocular membranes and structures within the eye.

2. A method according to claim 1 wherein said trypan blue solution contains 0.05% w/w to 3% w/w trypan blue.

3. A method according to claim 1 wherein said intraocular membrane is the epiretinal or internal limiting membrane of the retina.

4. A method according to claim 1 wherein said intraocular membranes are pathological membranes.

5. A method according to claim 4 wherein said membrane results from proliferative vitreoretinopathy.

6. A method according to claim 1 wherein following visual identification of a membrane, the membrane is surgically treated.

7. A method according to claim 6 wherein said surgical treatment is selected from removal, lifting, repositioning or reduction in size.

* * * * *